United States Patent
Rezach et al.

(10) Patent No.: US 11,432,851 B2
(45) Date of Patent: Sep. 6, 2022

(54) SURGICAL INSTRUMENT AND METHOD

(71) Applicant: Warsaw Orthopedic, Inc., Warsaw, IN (US)

(72) Inventors: William Alan Rezach, Covington, TN (US); Brian A. Butler, Millington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/167,415

(22) Filed: Feb. 4, 2021

(65) Prior Publication Data

US 2022/0240984 A1 Aug. 4, 2022

(51) Int. Cl.
*A61B 17/70* (2006.01)
*A61B 17/00* (2006.01)

(52) U.S. Cl.
CPC .. *A61B 17/708* (2013.01); *A61B 2017/00367* (2013.01)

(58) Field of Classification Search
CPC ............ A61B 17/7074; A61B 17/7076; A61B 17/7077; A61B 17/708; A61B 2017/00367

USPC .............................................. 606/86 A, 86 R
See application file for complete search history.

(56) References Cited

U.S. PATENT DOCUMENTS

2009/0228053 A1\* 9/2009 Kolb .................... A61B 17/708
606/151

\* cited by examiner

*Primary Examiner* — Eduardo C Robert
*Assistant Examiner* — Christina Negrellirodriguez
(74) *Attorney, Agent, or Firm* — Sorell, Lenna & Schmidt, LLP

(57) ABSTRACT

A surgical instrument includes a first member including an inner surface. A second member is movable relative to the first member and defines a first opening for disposal of a first implant support. The second member is disposable with the inner surface to define a second opening for movement of a second implant support relative to the inner surface and a third opening is configured for movement of a third implant support relative to the inner surface. The first implant support is fixed with the second member. Systems, spinal constructs, implants and methods are disclosed.

18 Claims, 6 Drawing Sheets

SURGICAL INSTRUMENT AND METHOD

TECHNICAL FIELD

The present disclosure generally relates to medical devices for the treatment of musculoskeletal disorders, and more particularly to a spinal implant system and a method for treating a spine.

BACKGROUND

Spinal disorders such as degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments may employ implants that are manipulated for engagement with vertebrae to position and align one or more vertebrae. This disclosure describes an improvement over these prior technologies.

SUMMARY

In one embodiment, a surgical instrument is provided. The surgical instrument includes a first member including an inner surface. A second member is movable relative to the first member and defines a first opening for disposal of a first implant support. The second member is disposable with the inner surface to define a second opening for movement of a second implant support relative to the inner surface and a third opening is configured for movement of a third implant support relative to the inner surface. The first implant support is fixed with the second member. In some embodiments, systems, spinal constructs, implants and methods are disclosed.

In one embodiment, the surgical instrument includes a rail including an inner surface and arcuate end portions. A plate is connected to the rail and defines a first opening for disposal of a first implant support. The plate is rotatable relative to the rail into a closed configuration to define a second opening for movement of a second implant support relative to the inner surface and a third opening for movement of a third implant support relative to the inner surface. The plate is engageable with the first implant support to resist and/or prevent the first implant support from moving relative to the plate.

In one embodiment, a surgical system is provided. The surgical system includes a first member including an inner surface. A second member is movable relative to the first member and defines a first opening. A first implant support, a second implant support and a third implant support are provided. The second member is movable relative to the inner surface into a closed configuration to define a second opening for movement of the second implant support relative to the inner surface and a third opening for movement of the third implant support relative to the inner surface. The first implant support is fixed with the second member. The implant supports are disposed in a configuration with the members for connection with bone fasteners attached with vertebrae for derotation of a spine including the vertebrae.

BRIEF DESCRIPTION OF THE DRAWINGS

The present disclosure will become more readily apparent from the specific description accompanied by the following drawings, in which.

DETAILED DESCRIPTION

Figure 1:
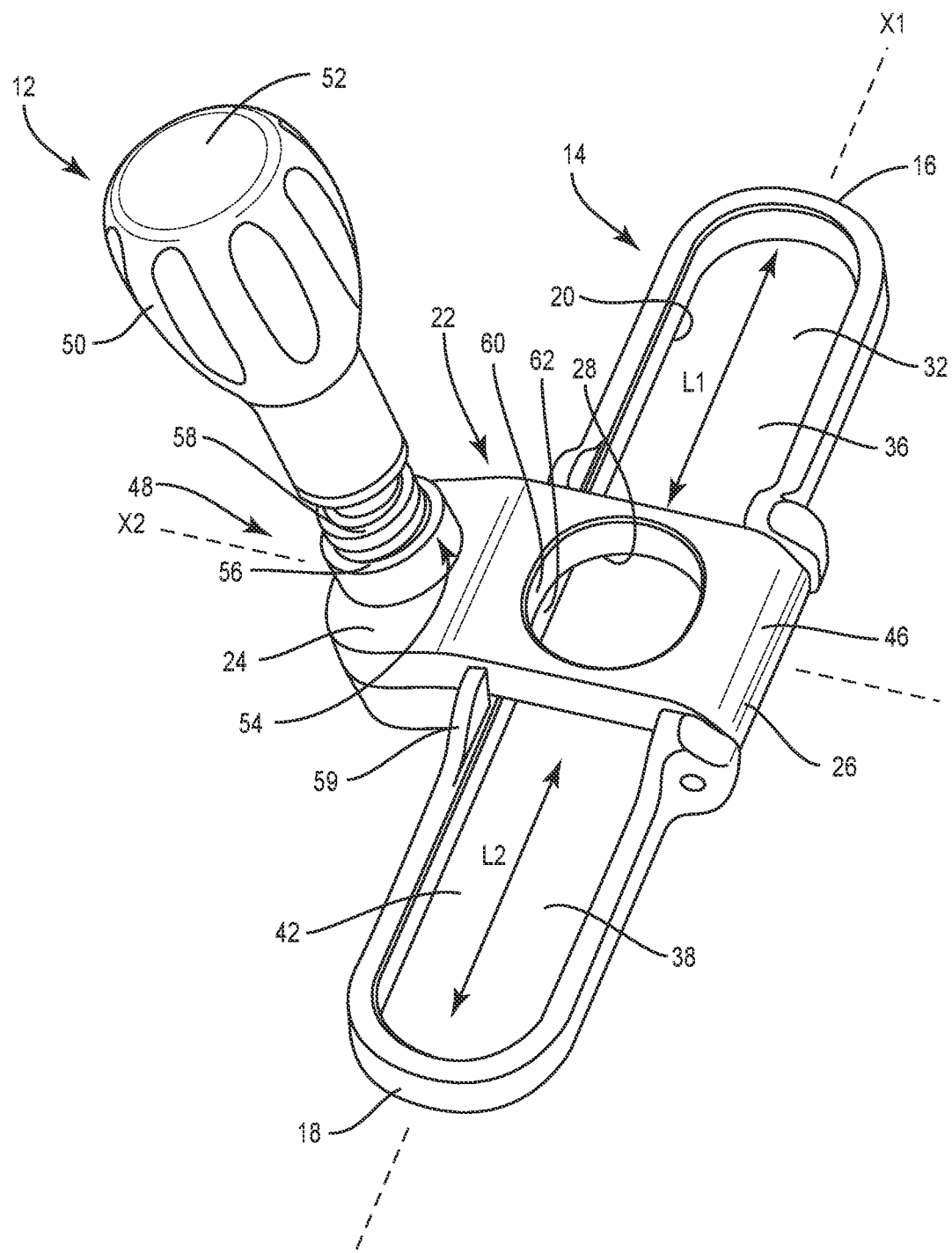
FIG. 1 is a perspective view of components of one embodiment of a surgical system in accordance with the principles of the present disclosure.

The exemplary embodiments of a surgical system and related methods of use disclosed are discussed in terms of medical devices for the treatment of musculoskeletal disorders and more particularly, in terms of a surgical system including one or more surgical instruments engageable with components of a spinal construct. In some embodiments, the present surgical system includes one or more surgical instruments and is employed with a method that facilitates kyphosing of the spine while simultaneously derotating the spine. In some embodiments, the systems and methods of the present disclosure are employed with a spinal deformity, joint fusion or fixation procedure, for example, with a cervical, thoracic, lumbar and/or sacral region of a spine.

In some embodiments, the present surgical system includes a surgical instrument that can be implemented in a spinal deformity procedure to derotate the spine and allows and/or accommodates kyphosing of the spine. In some embodiments, the present surgical system is employed for axial derotation of vertebral bodies to improve chest wall volume and pulmonary function. In some embodiments, the surgical instrument facilitates one or more rod reducers to slide along a spinal rod to implement kyphosing of the spine while a surgeon is derotating a spine. In some embodiments, the surgical instrument includes a first member, for example, a rail. In some embodiments, the rail includes an inner surface. In some embodiments, the surgical instrument includes a second member, for example, a plate. In some embodiments, the plate is movable relative to the rail and defines a first opening for disposal of a first implant support, for example, a first extender. In some embodiments, the plate is disposable with the inner surface to define a second opening for movement of a second implant support, for example, a second extender, relative to the inner surface. In some embodiments, a third opening is configured for movement of a third implant support, for example, a third extender relative to the inner surface. In some embodiments, the first extender is fixed with the plate.

In some embodiments, the present surgical instrument is configured to lock onto an implant support, for example, an extender. In some embodiments, the extender is locked centrally relative to the surgical instrument. In some embodiments, the surgical instrument is configured to retain one or more extenders. In some embodiments, the surgical instrument is configured to lock onto a central extender and to retain adjacent extenders. In some embodiments, the surgical instrument facilitates movement and/or translation of the adjacent extenders relative to the locked extender.

In some embodiments, the present surgical system includes a surgical instrument that is employed with a method to perform deformity correction procedures, for example, adolescent idiopathic scoliosis and adult deformity correction procedures that require rod reduction maneuvers. In some embodiments, the surgical system is employed with a method for deformity correction, for example, treatment of scoliosis. In some embodiments, the surgical system is configured for linking three extenders across a single vertebral body in a segmental configuration.

In some embodiments, the present surgical system includes a surgical instrument that is employed with a method of surgical treatment to correct a spinal deformity, for example, scoliosis. In some embodiments, the method includes the step of applying one or more extenders to concavity of a curve of a spine. In some embodiments, the method includes the step of connecting the surgical instrument to a portion of the one or more extenders. In some embodiments, the method includes the step of tightening the surgical instrument onto the one or more extenders. In some embodiments, the surgical instrument facilitates control of multiple vertebral levels simultaneously. In some embodiments, control of multiple vertebral levels simultaneously facilitates bone fastener implantation and/or bone fastener removal. In some embodiments, the surgical instrument derotates the spine and facilitates movement and/or translation of the one or more extenders to facilitate kyphosis.

In some embodiments, the surgical system may include instruments that are connected or attached to an extender(s), for example, a lateral translation handle or derotation instruments. In some embodiments, one or all of the components of the surgical system are disposable, peel-pack, pre-packed sterile devices used with a spinal correction system. In some embodiments, one or all of the components of the surgical system may be reusable. The surgical system may be configured as a kit with multiple sized and configured components.

In some embodiments, the surgical system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 can be employed, for example, with an open or mini-open, minimal access and/or minimally invasive including percutaneous surgical technique for engagement with an implant, for example, a bone fastener for a correction treatment at a surgical site within a body of a patient, for example, a section of a spine to treat various spine pathologies, for example, adolescent idiopathic scoliosis and Scheuermann's kyphosis. In some embodiments, one or more of the components of surgical system 10 are configured for engagement with spinal constructs, which may include spinal implants, for example, one or more rods, fasteners, plates and connectors. In some embodiments, the components of surgical system 10 are configured for engagement with existing spinal constructs attached with vertebrae in a revision surgery to manipulate tissue and/or correct a spinal disorder, as described herein.

Figure 2:
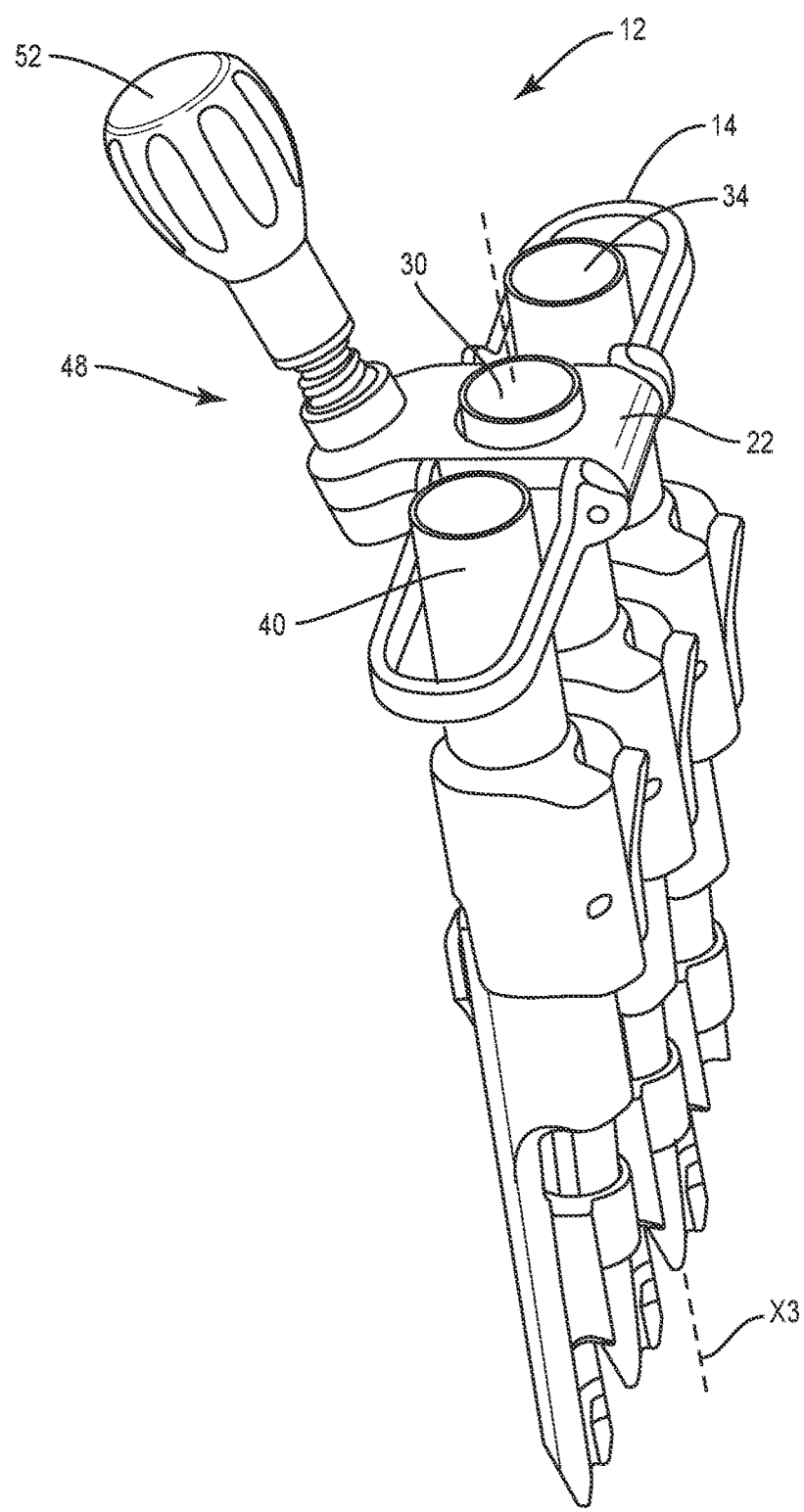
FIG. 2 is a perspective view of components of the system shown in FIG. 1.

Surgical system 10 includes a surgical instrument 12, as shown in FIGS. 1 and 2. Surgical instrument 12 is configured to engage with one or more implant supports to facilitate kyphosing and derotating of a spine, as described herein. Surgical instrument 12 includes a member, for example, a rail 14, as shown in FIG. 1. Rail 14 extends between an end portion 16, an end portion 18, and defines a longitudinal axis X1. End portions 16, 18 are arcuate. In some embodiments, end portions 16, 18 can be variously configured, for example, round, oval, oblong, square, rectangular, polygonal, irregular, uniform, non-uniform, offset, staggered, tapered, consistent or variable. Rail 14 includes an inner surface 20. In some embodiments, surface 20 may have various surface configurations, for example, rough, arcuate, undulating, mesh, porous, semi-porous, dimpled and/or textured.

Surgical instrument 12 includes a member, for example, a plate 22 connected to rail 14, as shown in FIG. 1. Plate 22 is movable relative to rail 14, as described herein. Plate 22 extends between an end 24, an end 26 and defines a longitudinal axis X2. Axis X2 is perpendicular relative to axis X1. A surface of plate 22 defines a centrally positioned opening 28 configured for disposal of an implant support, for example, an extender 30 that is disposed along a longitudinal axis X3, as shown in FIG. 2. Extender 30 is fixed with plate 22. Plate 22 is rotatable relative to rail 14 and is engageable with extender 30 to resist and/or prevent extender 30 from moving relative to plate 22. In some embodiments, opening 28 may have various surface configurations, for example, rough, arcuate, undulating, mesh, porous, semi-porous, dimpled and/or textured.

Plate 22 is configured for disposal with surface 20 of rail 14 to define an opening 32. Opening 32 is configured for movement of an implant support, for example, an extender 34 relative to surface 20. Opening 32 of rail 14 includes an elongated slot 36. Extender 34 is translatable within slot 36 relative to plate 22. Rail 14 includes a movable limit L1 for extender 34 that is disposed within slot 36 to translate within, described herein and shown in FIG. 1. In some embodiments, slot 36 may be variously configured, for example, round, oval, oblong, square, rectangular, polygonal, irregular, uniform, non-uniform, offset, staggered, tapered, consistent or variable.

Plate 22 is disposed with surface 22 of rail 14 to define an opening 38. Opening 38 opposes opening 32 and is configured for movement of an implant support, for example, an extender 40 relative to surface 20, as shown in FIGS. 1 and 2. Opening 38 of rail 14 includes an elongated slot 42. Extender 40 is translatable within slot 42 relative to plate 22. Rail 14 includes a movable limit L2 for extender 40 that is disposed within slot 42 to translate within, as described herein and shown in FIG. 1. In some embodiments, slot 42 may be variously configured, for example, round, oval, oblong, square, rectangular, polygonal, irregular, uniform, non-uniform, offset, staggered, tapered, consistent or variable.

Figure 5:
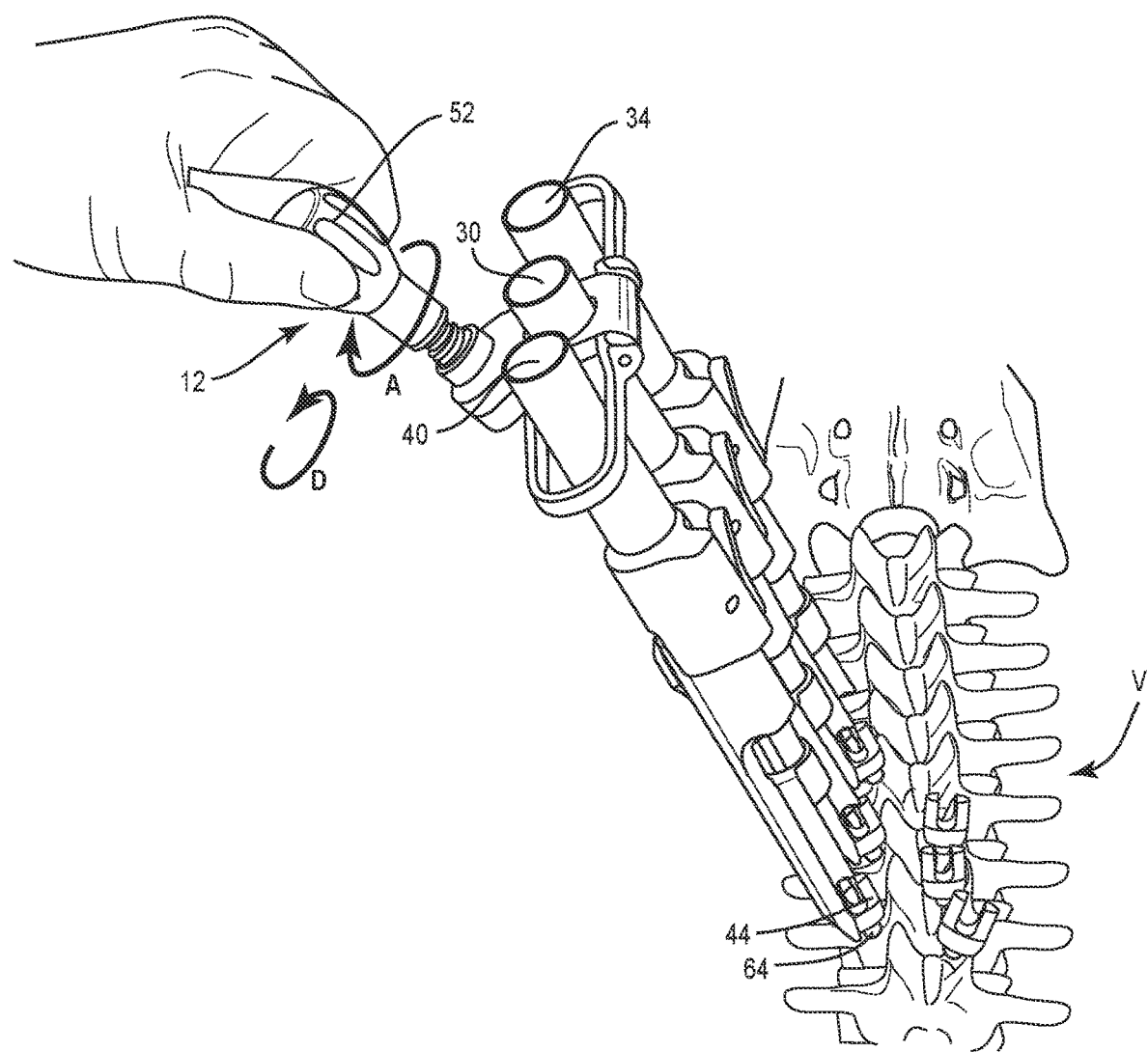
FIG. 5 is perspective view of components shown in FIG. 4 disposed with vertebrae.
Figure 6:
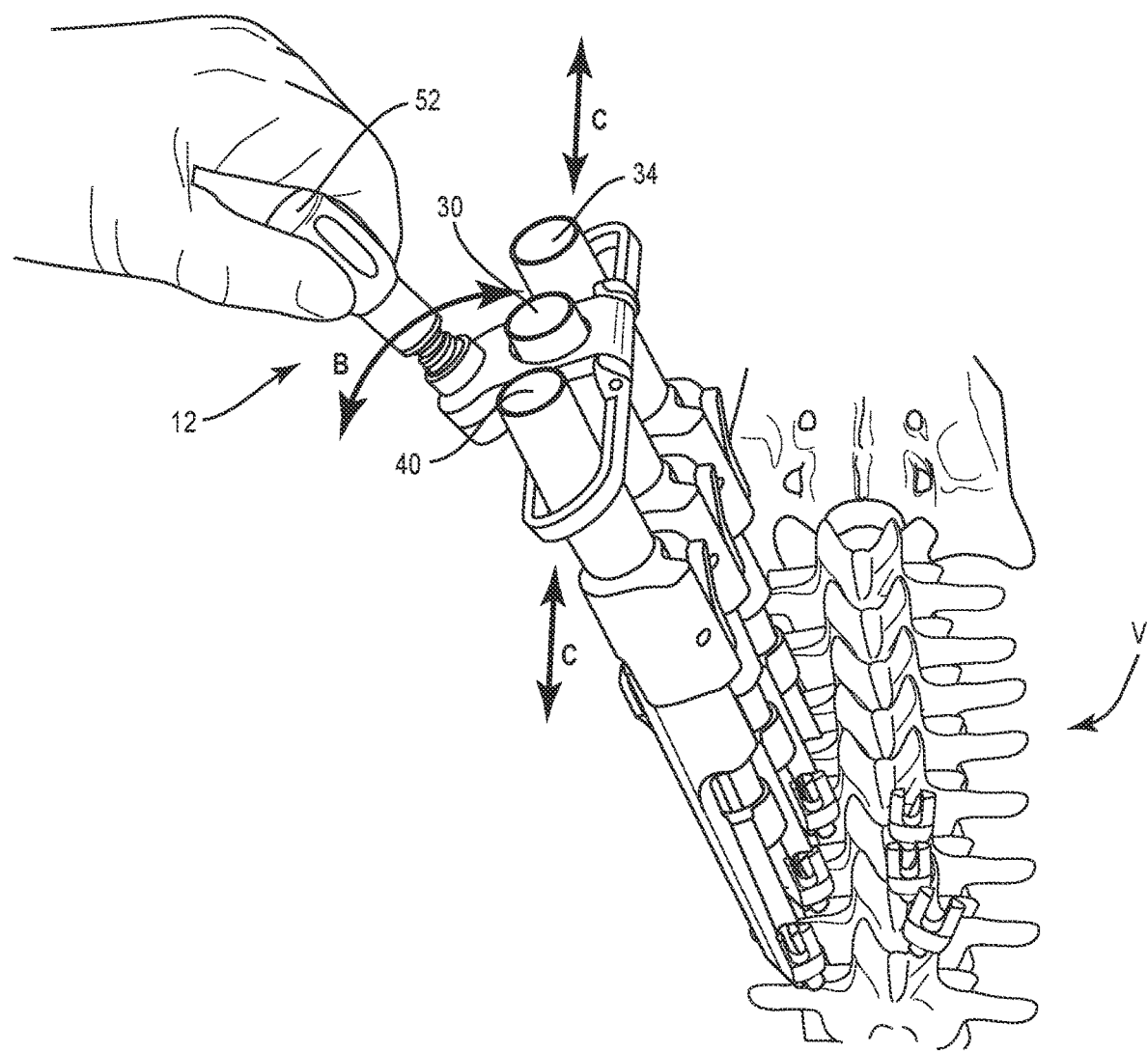
FIG. 6 is perspective view of components shown in FIG. 4 disposed with vertebrae.

Opening 28 of plate 22 is centrally positioned relative to openings 32 and 38, as shown in FIG. 1. Extenders 30,34 and 40 are disposed in a configuration with rail 14 and plate 22 for connection with bone fasteners 44 attached to vertebrae for derotation of a spine including the vertebrae, as shown in FIG. 5 and described herein. Plate 22 is connected to rail 14 via a hinge 46 disposed at end 26, as shown in FIG. 1. Hinge 46 extends along axis X1.

Plate 22 includes a clamping mechanism 48. Clamping mechanism 48 is configured to facilitate rotation of plate 22 relative to rail 14 between an open configuration and a closed configuration such that extender 30 is resisted and/or prevented from moving relative to plate 22. In the open configuration, clamping mechanism 48 is free to travel along axis X3 of extender 30 and extender 30 is movable within opening 28 of plate 22. In the closed configuration, clamping mechanism 48 is secured with frictional force on extender 30 to resist and/or prevent movement along axis X3 of extender 30 and to forcibly engage, resist and/or prevent extender 30 from moving relative to plate 22, as described herein. Clamping mechanism 48 includes an actuator 50. Actuator 50 includes a handle 52 that is connectable with plate 22 and rail 14. In some embodiments, handle 52 may have various cross-section configurations, for example, cylindrical, oval, oblong, triangular, rectangular, square, polygonal, irregular, uniform, non-uniform, variable, tubular and/or tapered. In some embodiments, handle 52 includes one or more of various surface configurations, for example, rough, threaded, arcuate, undulating, porous, semi-porous, dimpled, polished and/or textured.

Actuator 50 includes a screw jack 54 connected with rail 14 and plate 22 via a threaded opening 56 and is configured to fix rail 14 and plate 22 in the closed configuration. Screw jack 54 includes a lead screw 58 and a spherical interface (not shown) between lead screw 58 and rail 14. The spherical interface is configured to facilitate pivoting motion when lead screw 58 is rotated via handle 52. A guide element 59 of rail 14 is configured to substantially align plate 22 with rail 14 in the closed configuration. In the closed configuration, lead screw 58 is actuated by handle 52 via rotation of handle 52 to engage a wall 60 of plate 22 and a wall 62 of rail 14. Lead screw 58 applies a force to walls 60, 62 to drive walls 60, 62 into frictional engagement with a surface of extender 30 to forcibly engage, resist and/or prevent extender 30 from moving relative to plate 22, as shown in FIG. 5. In the closed configuration, plate 22 is biased to the closed configuration and opening 32 is separate and spaced apart from opening 38. In the open configuration, walls 60, 62 are not driven into engagement with a surface of extender 30 and extender 30 is movable within opening 28 of plate 22. In some embodiments, actuator 50 can include, for example, a spring or other manual actuation.

In operation, the components of surgical system 10 are disposable in an open configuration and a closed configuration. In the open configuration, no appreciable force is applied to extender 30, and extenders 34, 40 are translatable within slots 36 and 42 relative to plate 22 respectively. In some embodiments, extenders 34, 40 can be selectively translated along slots 36, 42 and/or positioned at a selected orientation. Handle 52 is rotated in a direction, for example, a clockwise direction, shown by arrow A in FIG. 5, and lead screw 58 is actuated to engage and apply a force to walls 60, 62 to drive walls 60, 62 into frictional engagement with a surface of extender 30 to forcibly engage, resist and/or prevent extender 30 from moving relative to plate 22. In the closed configuration, extenders 34,40 are retained within slots 36, 42 respectively. Surgical instrument 12 can then be translated in a direction, shown by arrow B in FIG. 6 to derotate a selected section of a spine. Extenders 34, 40 are translatable within slots 36, 42, as shown by arrows C in FIG. 6 during derotation to facilitate kyphosis.

Extender 30 is released from the closed configuration. Handle 52 is rotated in a direction, for example, a counter clockwise direction shown by arrow D in FIG. 5, and lead screw 58 is actuated to disengage from walls 60, 62, thereby releasing extender 30 from frictional engagement.

In assembly, operation and use, surgical system 10, similar to the system described above, is employed with a surgical procedure, for example, a correction treatment to treat adolescent idiopathic scoliosis and/or Scheuermann's kyphosis of a spine. In some embodiments, one or all of the components surgical system 10 can be delivered or utilized as a pre-assembled device or can be assembled in situ.

Figure 3:
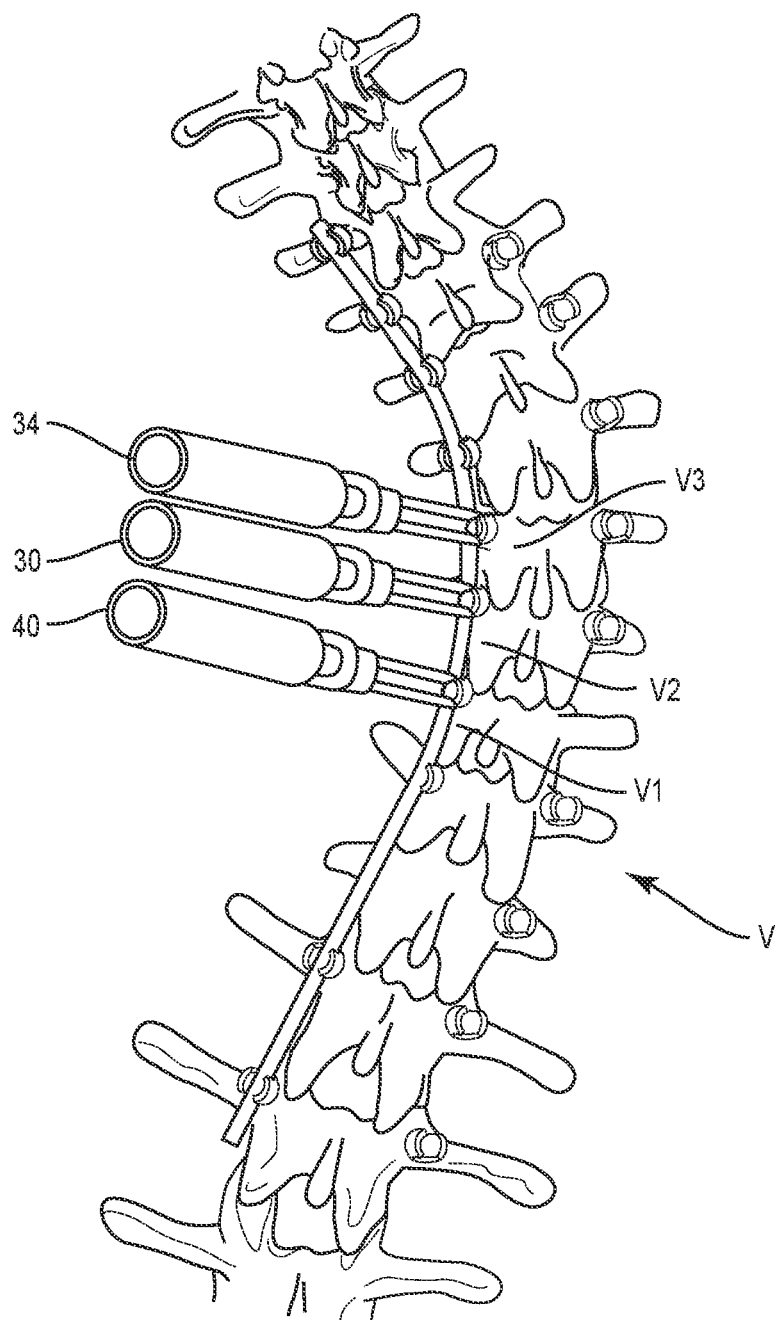
FIG. 3 is a perspective view of components of one embodiment of a surgical system in accordance with the principles of the present disclosure disposed with vertebrae.

For example, surgical system 10 can be employed with a surgical correction treatment of an applicable condition or injury of an affected section of a spinal column and adjacent areas within a body, for example, vertebral levels V1, V2, V3 of vertebrae V, as shown in FIG. 3. In some embodiments, surgical system 10 may be employed with one or a plurality of vertebrae.

An incision is made in the body of a patient and a cutting instrument (not shown) creates a surgical pathway. A preparation instrument (not shown) can be employed to prepare tissue surfaces of or surrounding vertebrae V, as well as for aspiration and irrigation of a surgical region. Pilot hole(s) (not shown) are made with the selected areas of bone, for example vertebrae V for receiving a shaft 64 of bone fastener 44, as shown in FIG. 5.

Figure 4:
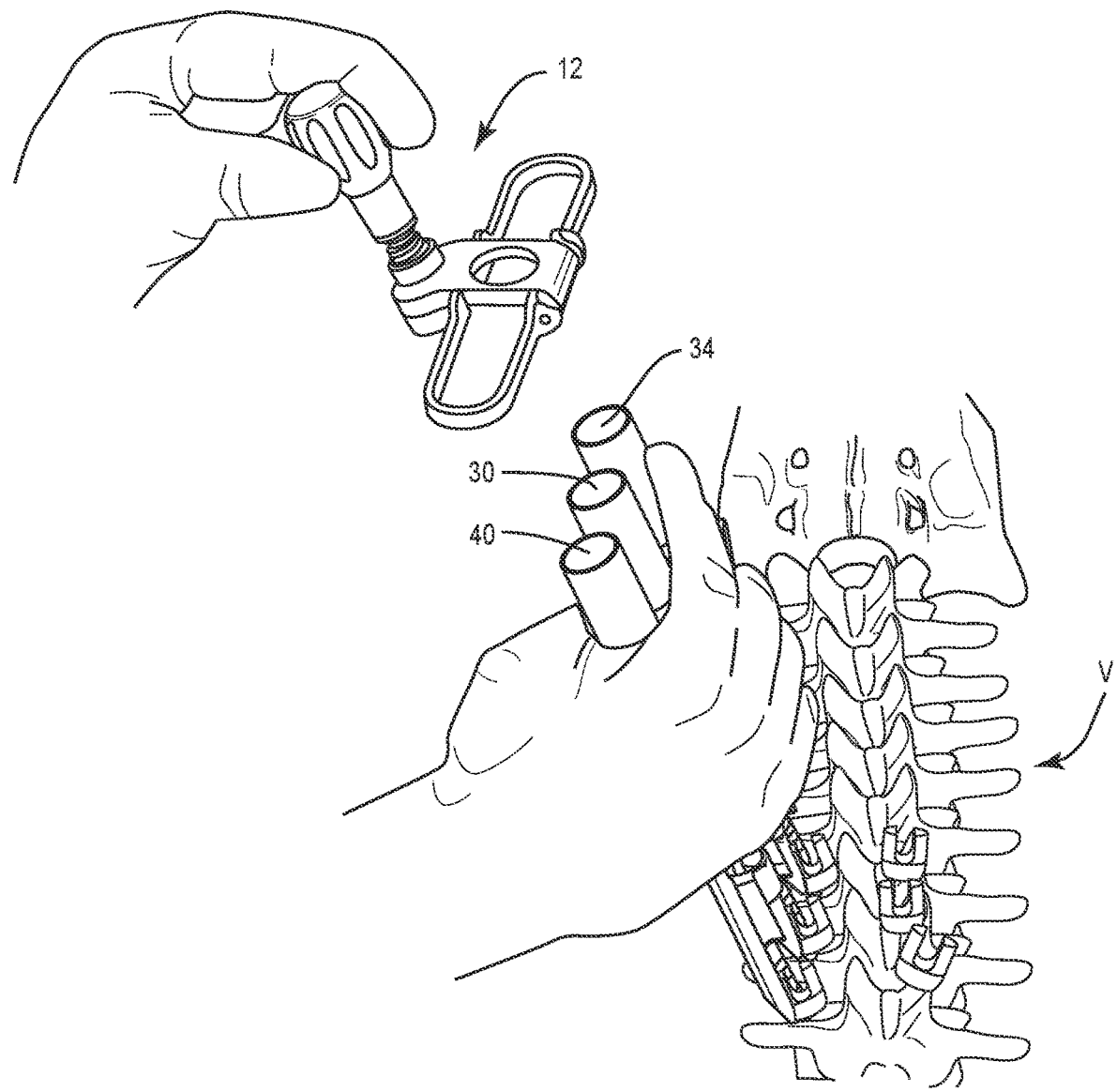
FIG. 4 is perspective view of components of one embodiment of a surgical system in accordance with the principles of the present disclosure disposed with vertebrae.

Extenders 30, 34 and 40 are attached to bone fasteners 44, as shown in FIG. 3. Surgical instrument 12 is disposed over extenders 30, 34, and 40, as shown in FIG. 4. Surgical instrument 12 is placed in the closed configuration by rotating handle 52 in a clockwise direction, shown by arrow A in FIG. 5, and lead screw 58 is actuated to engage and apply a force to walls 60, 62 to drive walls 60, 62 into frictional engagement with a surface of extender 30 to forcibly engage, resist and/or prevent extender 30 from moving relative to plate 22. Surgical instrument 12 is translated in a direction, shown by arrow B in FIG. 6 to derotate a selected section of a spine. Extenders 34, 40 are translatable within slots 36, 42, as shown by arrows C in FIG. 6 during derotation to facilitate kyphosis.

Extender 30 is released from the closed configuration. Handle 52 is rotated in a counter clockwise direction shown by arrow D in FIG. 5, and lead screw 58 is actuated to disengage from walls 60, 62, thereby releasing extender 30 from frictional engagement.

Upon completion of a procedure, surgical instrument 12, additional surgical instruments and/or tools, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10.

In some embodiments, surgical system 10 may include one or a plurality of plates, connectors and/or bone fasteners for use with a single vertebral level or a plurality of vertebral levels. In some embodiments, one or more of bone fasteners may be engaged with tissue in various orientations, such as, for example, series, parallel, offset, staggered and/or alternate vertebral levels. In some embodiments, one or more bone fasteners may comprise multi-axial screws, sagittal angulation screws, pedicle screws, mono-axial screws, uniplanar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member defining a longitudinal axis and including an inner surface; and
   a second member being movable relative to the first member and defining a centrally disposed first opening for disposal of a first implant support, the second member being fixed with the first member relative to the longitudinal axis,
   the second member being attached with the inner surface to define a second opening for translation of a second implant support along the longitudinal axis relative to the inner surface and a third opening for translation of a third implant support along the longitudinal axis relative to the inner surface, and the first implant support being fixed with the second member,
   the second member being rotatable relative to the first member between an open configuration and a closed configuration such that the first implant support is resisted and/or prevented from moving relative to the second member, the second member being biased to the closed configuration.

2. A surgical instrument as recited in claim 1, wherein the implant supports are disposed in a configuration with the members for connection with bone fasteners attached with vertebrae for derotation of a spine including the vertebrae.

3. A surgical instrument as recited in claim 1, wherein the second member is rotatable relative to the first member and engageable with the first implant support to resist and/or prevent the first implant support from moving relative to the second member.

4. A surgical instrument as recited in claim 1, wherein the second opening includes an elongated slot and the second implant support is translatable in the slot relative to the second member.

5. A surgical instrument as recited in claim 4, wherein the third opening includes an elongated slot and the third implant support is translatable in the slot relative to the second member.

6. A surgical instrument as recited in claim 1, wherein the first opening is centrally positioned relative to the second opening and the third opening.

7. A surgical instrument as recited in claim 1, wherein the second member is connected to the first member via a hinge.

8. A surgical instrument as recited in claim 1, wherein the first member includes at least one guide element configured to substantially align the second member with the first member in the closed configuration.

9. A surgical instrument as recited in claim 1, wherein the second opening is separate and spaced apart from the third opening in the closed configuration.

10. A surgical instrument as recited in claim 1, further comprising an actuator including a handle and being connectable with the members.

11. A surgical instrument as recited in claim 10, wherein the actuator includes a screw jack connected with the members and configured to fix the members in the closed configuration.

12. A surgical instrument as recited in claim 1, wherein the first member includes at least one rail having the inner surface and defining the second opening and the third opening.

13. A surgical instrument as recited in claim 12, wherein the rail includes a movable limit for the second implant support in the second opening and a movable limit for the third implant support in the third opening.

14. A surgical instrument as recited in claim 1, wherein the second member includes a plate defining the first opening.

15. A surgical instrument comprising:
    a rail including an inner surface and arcuate end portions, the rail defining a longitudinal axis; and
    a plate attached to the rail and fixed therewith relative to the longitudinal axis, the plate being movable along a transverse axis and defining a centrally disposed first opening for disposal of a first implant support,
    the plate being rotatable relative to the rail into a closed configuration to define a second opening for translation of a second implant support along the longitudinal axis relative to the inner surface and a third opening for translation of a third implant support along the longitudinal axis relative to the inner surface, and
    the plate being engageable with the first implant support to resist and/or prevent the first implant support from moving relative to the plate.

16. A surgical instrument as recited in claim 15, wherein the first opening is centrally positioned relative to the second opening and the third opening.

17. A surgical instrument as recited in claim 15, wherein the rail includes a movable limit for the second implant support in the second opening and a movable limit for the third implant support in the third opening.

18. A surgical system comprising:
    a first member defining a longitudinal axis and including an inner surface;
    a second member being movable along a transverse axis relative to the first member and defining a centrally disposed first opening, the second member being fixed with the first member relative to the longitudinal axis; and
    a first implant support, a second implant support and a third implant support,
    the second member being movable relative to the inner surface into a closed configuration to define a second opening for translation of the second implant support along the longitudinal axis relative to the inner surface and a third opening for translation of the third implant support along the longitudinal axis relative to the inner surface, and the first implant support being fixed with the second member,
    the implant supports being disposed in a configuration with the members for connection with bone fasteners attached with vertebrae for derotation of a spine including the vertebrae.

* * * * *